United States Patent [19]
Kato et al.

[11] Patent Number: 5,928,494
[45] Date of Patent: Jul. 27, 1999

[54] GAS SENSOR AND METHOD OF MEASURING QUANTITY OF SPECIFIC COMPOUNDS IN MEASURING GAS

[75] Inventors: Nobuhide Kato, Ama-gun; Noriyuki Ina, Okazaki, both of Japan

[73] Assignee: NGK Insulators, Ltd., Japan

[21] Appl. No.: 08/818,715

[22] Filed: Mar. 14, 1997

[30] Foreign Application Priority Data

Mar. 25, 1996 [JP] Japan .................................. 8-067755
Feb. 28, 1997 [JP] Japan .................................. 9-045050

[51] Int. Cl.$^6$ .................................................. G01N 27/407
[52] U.S. Cl. ........................ 205/781; 204/425; 204/426; 205/784.5
[58] Field of Search ........................... 204/408, 421–429; 205/783.5, 784, 784.5, 785, 781

[56] References Cited

U.S. PATENT DOCUMENTS

| | | | |
|---|---|---|---|
| 4,464,646 | 8/1984 | Burger et al. | 338/25 |
| 4,471,648 | 9/1984 | Uchida et al. | 204/408 |
| 4,505,783 | 3/1985 | Mase et al. | 204/425 |
| 4,505,804 | 3/1985 | Mase et al. | 204/425 |
| 4,634,514 | 1/1987 | Nishizawa et al. | 204/406 |
| 4,875,990 | 10/1989 | Kodachi et al. | 204/427 |
| 4,963,246 | 10/1990 | Nakajima et al. | 204/408 |
| 5,017,340 | 5/1991 | Pribat et al. | 204/424 |
| 5,173,166 | 12/1992 | Tomantschger et al. | 204/425 |
| 5,234,569 | 8/1993 | Hunt | 204/425 |
| 5,338,431 | 8/1994 | Yorita et al. | 204/424 |
| 5,391,284 | 2/1995 | Hotzel | 204/427 |
| 5,397,442 | 3/1995 | Wachsman | 204/426 |
| 5,430,428 | 7/1995 | Gerblinger et al. | 338/25 |
| 5,676,811 | 10/1997 | Makino et al. | 204/427 |

FOREIGN PATENT DOCUMENTS

| | | |
|---|---|---|
| 0 480 076 A1 | 4/1992 | European Pat. Off. . |
| 0 678 740 A1 | 10/1995 | European Pat. Off. . |
| WO 94/20842 | 9/1994 | WIPO . |

OTHER PUBLICATIONS

Hackh's Chemical Dictionary, 1969, p. 607.

Primary Examiner—T. Tung
Attorney, Agent, or Firm—Parkhurst & Wendel

[57] ABSTRACT

A gas sensor for measuring a quantity of specific component in a measuring gas includes a main pump means which has an electrochemical pump cell. The electrochemical pump cell includes a solid electrolyte partition exposed to external space, an inner pump electrode and an outer pump electrode formed on the inner surface and outer surface of the solid electrolyte partition, respectively. The main pump means treats oxygen contained in the measuring gas introduced from the outer space by pumping processing on the basis of a control voltage applied between the inner pump electrode and the outer pump electrode. An RLC element which has a specific electric characteristic value corresponding to a characteristic value of the electrochemical pump cell is connected in parallel with the electrochemical pump cell.

4 Claims, 4 Drawing Sheets

GAS SENSOR AND METHOD OF MEASURING QUANTITY OF SPECIFIC COMPOUNDS IN MEASURING GAS

BACKGROUND OF THE INVENTION

1. Field of the Invention

The present invention relates to a gas sensor for measuring a quantity of specific component in a measuring gas and a method of measuring thereof. More specifically, the present invention is directed to a gas sensor and a method capable of accurately and readily correcting a dispersion in output characteristics among sensors.

2. Description of Related Art

Hitherto, there is known a method of measuring a quantity of specific component such as oxygen gas, in which an electrochemical pump cell including a partition made of solid electrolyte such as a zirconia ceramic and provided with a pair of electrodes thereon is used, and the diffusion limiting current is measured when applying current between these electrodes. In the method, the diffusion limiting current varies with the difference in the structure of sensor element, particularly with the dispersion of the microstructure of electrode and of the porosity in gas diffusion resistance layer. Accordingly, accurate measurement needs to apply a correction responding to the sensitivity of individual sensor elements.

Different from the sensors used in analyzers, there is a problem on correcting the dispersion among sensors as automobile parts. That is, dispersion among individual sensors in terms of sensor characteristic is not able to be adjusted from the interface side.

Consequently, sensors mounted on an automobile require any means to correct the dispersion among individual sensors.

For correcting that type of dispersion among the individual sensors, there are known methods such as:

1) a method, as shown in FIG. 8, in which a diffusion limiting current is divided into two routes using two resistors, 32 and 33, to adjust the diffusion limiting current to a predetermined value; and 2) a method in which after measuring the respective sensor characteristics, the measured characteristics are ranked, then as shown in FIG. 7, the fixed resistor 12 having a resistance value corresponding to each rank is built in the connector casing.

The method illustrated in FIG. 8 is configured by a circuit which comprises: an electrochemical pump cell 60 including a solid electrolyte partition 2, a pair of electrodes 3 and 4 formed on the inner surface and outer surface thereof, and a gas diffusion resistance layer 5 formed on the electrode 3; a power source 9; and a current detection means 10 both of which are arranged between output terminals 6 and 7 of the electrochemical pump cell 60, wherein a diffusion limiting current to be flowed to the electrochemical pump cell 60 is divided by the resistors 32 and 33, to thereby flow the current proportional to the concentration of the specific component in the measuring gas to the current detection means 10.

Further, according to a method shown in FIG. 7, a sensor is configured by a circuit which comprises: an electrochemical pump cell 60 including a solid electrolyte partition 2, a pair of electrodes 3 and 4 formed on the inner surface and outer surface thereof, and a gas diffusion resistance layer 5 formed on the electrode 3; a power source 9; and a current detection means 10 both of which are arranged between output terminals 6 and 7 of the electrochemical pump cell 60, wherein after measuring the characteristic thereof, the measured characteristic is ranked. Subsequently, as shown in FIG. 7, a connector casing in which a fixed resistor 12 corresponding to each rank is built and is combined with the electrochemical pump cell 60 to detect the current by a separate current detection means 15 which is connected to the fixed resistor 12 in series.

However, for a sensor having shunt resistors or a sensor having a fixed resistor responding to each rank, both of which are described above, they have disadvantages such that the number of terminals on the connector increases, the reliability decreases and the production cost increases.

SUMMARY OF THE INVENTION

In view of the above, it is an object of the present invention to provide a correction method that can solve the problems of the conventional correction methods.

To attain the above-described object, according to the present invention, there is provided a gas sensor for measuring a quantity of specific component in a measuring gas comprising: a main pump means including an electrochemical pump cell comprising a solid electrolyte partition exposed to external space, an inner pump electrode and an outer pump electrode formed on the inner surface and outer surface of the solid electrolyte partition, respectively, and said main pump means treating oxygen contained in the measuring gas introduced from said external space by pumping processing on the basis of a control voltage applied between said inner pump electrode and said outer pump electrode, wherein an RLC element which has a predetermined electric characteristic value corresponding to a characteristic value of said electrochemical pump cell is connected in parallel with said electrochemical pump cell.

Further, according to the present invention, there is provided a gas sensor for measuring a quantity of a specific component in a measuring gas comprising: a main pump means including an electrochemical pump cell comprising a solid electrolyte partition exposed to external space, an inner pump electrode and an outer pump electrode formed on the inner surface and outer surface of the solid electrolyte partition, respectively, and said main pump means treating oxygen contained in the measuring gas introduced from said external space by pumping processing on the basis of a control voltage applied between said inner pump electrode and said outer pump electrode; and an electric signal conversion means for generating an electric signal corresponding to the quantity of oxygen generated by decomposition or reduction of the target component contained in the measuring gas after treated by the pumping processing by said main pumping means in which one side thereof has a pair of detection electrodes formed on the side where the measuring gas that was treated by pumping processing by said main pumping means is introduced, wherein an RLC element which has a predetermined electric signal characteristic value corresponding to an electric characteristic value of said gas sensor is connected in parallel with the output terminals of either said electrochemical pump cell or said electric signal conversion means.

In the present invention, the electric signal conversion means preferably comprises a measuring pump means for conducting the pumping processing of oxygen generated by decomposition or reduction of target components contained in the measuring gas after treated by the pumping processing by the main pumping means on the basis of a measuring voltage applied between the pair of detection electrodes, and a current detection means for detecting pump current generated in the measuring pump means. In this case, a quantity of specific component in the measuring gas is determined on the basis of the pump current detected by the current detection means.

Further, the electric signal conversion means preferably comprises a concentration detection means for generating an electromotive force corresponding to the difference between a quantity of oxygen generated by the decomposition or the reduction of a target component contained in the measuring gas after treated by the pumping processing by the main pumping means and a quantity of the oxygen contained in a reference gas on the side of detection electrode formed on the side of reference gas, and a voltage detection means for detecting the electromotive force generated in the concentration detection means. In this case, a quantity of the specific component in the measuring gas is determined on the basis of the electromotive force detected by the voltage detection means.

Still further, according to the present invention, there is provided a method of measuring a quantity of specific component in a measuring gas comprising: using a main pump means of a sensor including an electrochemical pump cell comprising a solid electrolyte partition exposed to the external space, an inner pump electrode and an outer pump electrode formed on the inner surface and the outer surface of said solid electrolyte partition, respectively, to control the oxygen gas partial pressure in the measuring gas to a predetermined value by conducting the pumping processing of the oxygen contained in the measuring gas which is introduced from the external space on the basis of a control voltage applied between said inner pump electrode and said outer pump electrode, wherein an RLC element which has a predetermined electric characteristic value corresponding to a characteristic value of said electrochemical pump cell is connected in parallel with said electrochemical pump cell while connecting both ends of the RLC element to the output terminals of the sensor; setting of the output correction of said electrochemical pump cell at an elevated temperature is carried out at room temperature by measuring the electric characteristic value of said RLC element in a state that ion conductivity of solid electrolyte is removed; and the output of said electrochemical pump cell is corrected on the basis of the set value.

Furthermore, according to the present invention, there is provided a method of a measuring a quantity of specific component in a measuring gas comprising: using a main pump means of a sensor including an electrochemical pump cell comprising a solid electrolyte partition exposed to the external space, an inner pump electrode and an outer pump electrode formed on the inner surface and the outer surface of the solid electrolyte partition, respectively, to control the oxygen gas partial pressure in the measuring gas to a predetermined value by conducting the pumping processing of the oxygen contained in the measuring gas introduced from the external space on the basis of a control voltage applied between said inner pump electrode and said outer pump electrode; converting a target component contained in the measuring gas after treated by the pumping processing by said main pump means using an electric signal conversion means in which one side thereof has a pair of detection electrodes formed on the side where the measuring gas that was treated by the pumping processing by said main pumping means into an electric signal corresponding to a quantity of oxygen generated either by decomposition or reduction; and measuring a quantity of specific component in the measuring gas on the basis of an electric signal coming from said electric signal conversion means, wherein an RLC element which has a predetermined electric characteristic value corresponding to a characteristic value of said electric signal is connected in parallel with the output terminal of either said electrochemical pump cell or said electric signal conversion means while connecting both ends of the RLC element to the output terminals of the sensor; the setting of the output correction of said electric signal conversion means at an elevated temperature is carried out at room temperature by determining an electric characteristic value of said RLC element in a state that the ion conductivity of the solid electrolyte is removed; and the output of said electric signal conversion means is corrected on the basis of the set value.

As described above, the present invention relates to an improvement of the above-described conventional method 2). According to the present invention, the interface mounted on an automobile stores the correction value corresponding to each rank, thus reading the label on the sensor side before actuating the sensor, and selecting an adequate correction value to correct the sensor output.

It should be noted that according to the present invention, the RLC element is preferably a resistor (R), also the RLC element is preferably either a capacitor (C), a series circuit of a capacitor (C) and a resistor (R), or a series circuit of a capacitor (C) and an inductor (L). Furthermore, other than the combination of these resistor, capacitor, and inductor as an RLC element, an oscillator or a filter which has a maximum or a minimum value at a specific frequency may be used.

DETAILED DESCRIPTION OF THE PREFERRED EMBODIMENT

Figure 1:
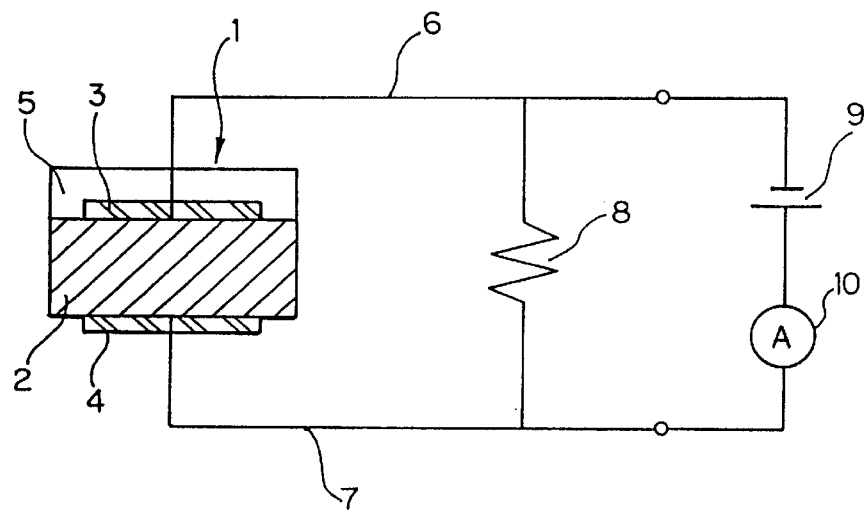
FIG. 1 is a cross sectional view of a main part of a sensor element and a circuit showing an example of a basic structure according to the present invention.

FIG. 1 is a diagram showing a circuit illustrating an example of a basic structure according to the present invention. An electrochemical pump cell 1 is made up of a solid electrolyte partition 2 comprising such as a zirconia ceramic which shows substantially no ion conductivity at room temperature and which shows ion conductivity at an elevated temperature, a pair of electrodes 3 and 4 formed on the inner surface and the outer surface of the solid electrolyte partition 2, respectively, and a gas diffusion resistance layer 5 formed on the electrode 3. A resistor 8 having a resistance corresponding to the sensitivity of the cell is connected to output terminals 6 and 7 of the electrochemical pump cell 1 in parallel therewith.

In the above-described configuration of the sensor circuit, when a predetermined voltage (control voltage) is applied from a power source 9 to the output terminals 6 and 7 of the electrochemical pump cell 1, almost no current flows to the cell 1 because the impedance of the cell 1 is very high at room temperature, and the current flows substantially only to a fixed resistor 8. Accordingly, if the measurement of the current is conducted by a current detection means 10, the resistance value of the fixed resistor 8 can be read. Since the resistance value is set to correspond to the sensitivity of each cell, information relating to the resistance value of the cell is stored in the current detection means 10 that measures the current flowing across the cell, thereby being capable of correcting the value of the current in the case of the cell actuation at an elevated temperature based on the equation given below:

$$I_0 = K_n(I_n - V/R_n)$$

where, $I_0$ is the diffusion limiting current after correcting sensitivity, $K_n$ is the correction factor corresponding to the sensitivity of each cell, $I_n$ is the value of current flowing across the current detection means 10, $R_n$ is the resistance of the fixed resistor 8, and V is the voltage at the power source 9.

It should be noted that the internal resistance of the current detection means 10 is assumed as negligible or small.

Figure 3:
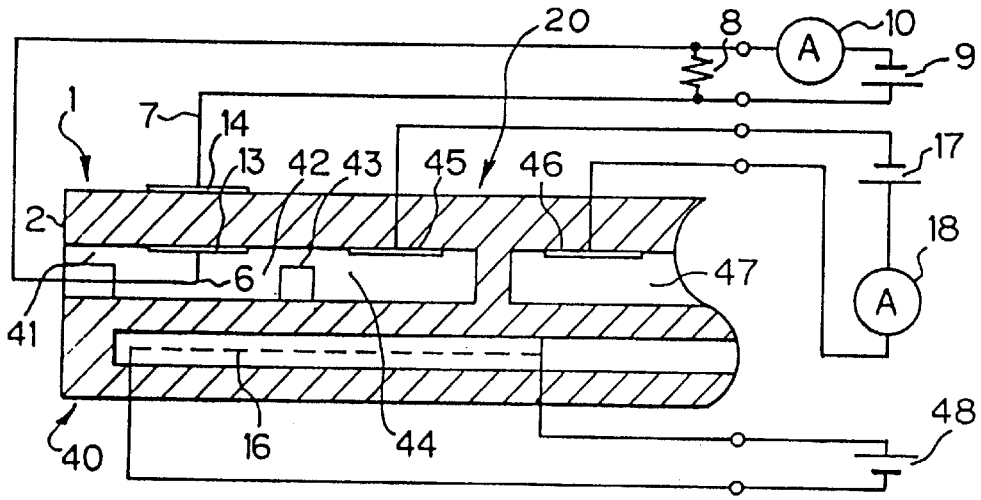
FIG. 3 is a cross sectional view of the main part of the sensor element and the circuit showing an example according to the present invention.
Figure 4:
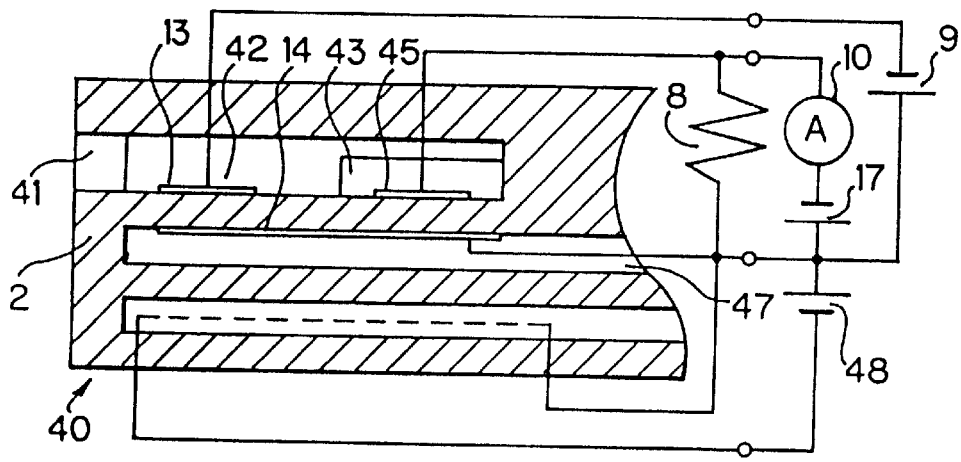
FIG. 4 is a cross sectional view of the main part of the sensor element and the circuit showing another example according to the present invention.
Figure 5:
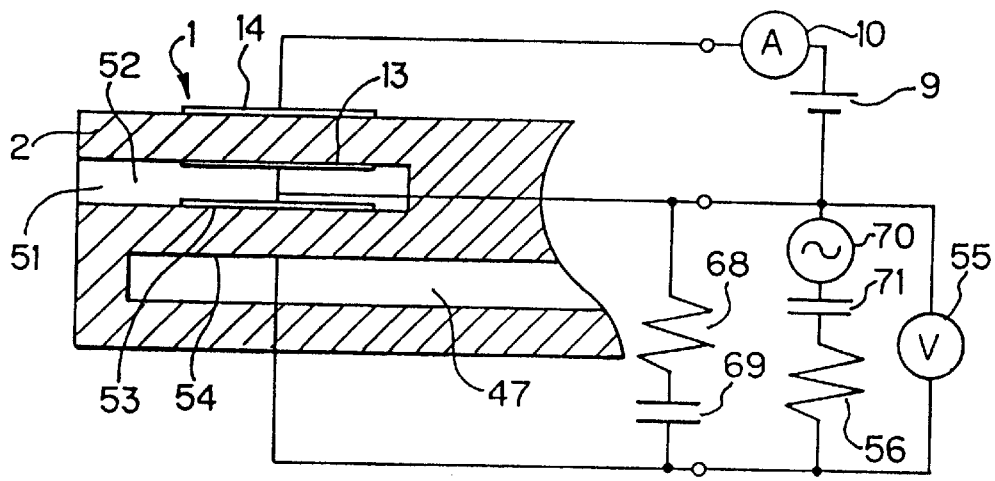
FIG. 5 is a cross sectional view of the main part of the sensor element and the circuit showing further another example according to the present invention.

The sensitivity of the cell (sensor output) and the offset value are examples of the characteristic values of an electrochemical pump cell (the electric signal characteristic of the sensor in the case of including an electric signal conversion means as shown in FIG. 3 through FIG. 5, described later) represented by the electric characteristic value of an RLC element as a resistor in FIG. 1.

Examples of the sensitivity of cell (sensor output) are:

(1) rate of the increase in a pump current relative to the concentration of specific component in the measuring gas;

(2) rate of the reduction of an electromotive force relative to the concentration of specific component in the measuring gas; and (3) rate of the change in a resistance relative to the concentration of a specific component in the measuring gas.

Examples of offset value of a cell (sensor output) are:

(1) a pump current value flowing at zero concentration of a specific component in the measuring gas;

(2) an electromotive force generated at zero concentration of a specific component in the measuring gas; and (3) a resistance at zero concentration of a specific component in the measuring gas.

As a result, $I_0$ in FIG. 1 becomes a value after correcting the dispersion of sensitivity in each cell, thus $I_0$ and the composition of the measuring gas have a very close correlation with each other. The fixed resistor 8 may be configured with thermet as the resistor sintered onto the sensor element, or may be contained in the connector casing of the sensor.

Figure 2:
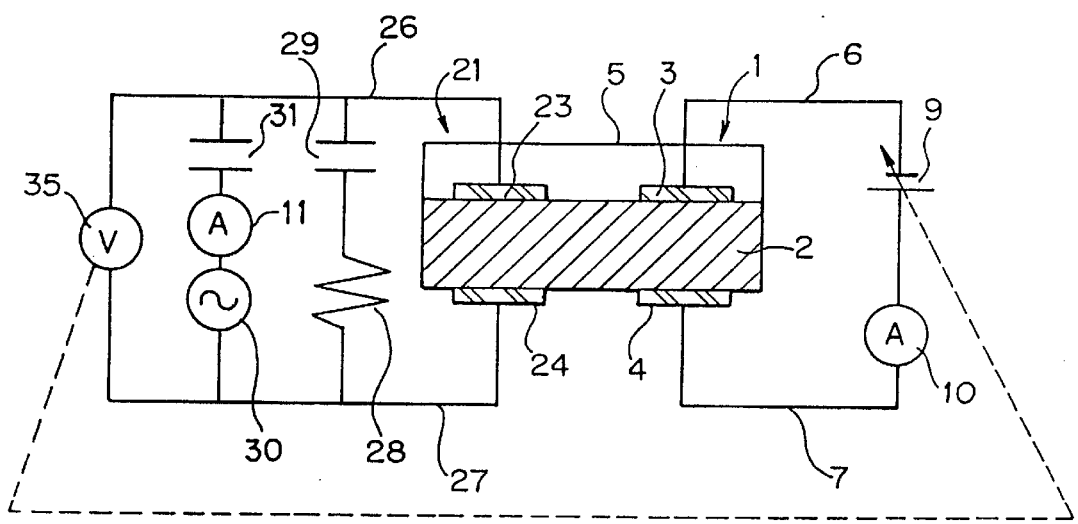
FIG. 2 is a cross sectional view of the main part of the sensor element and the circuit showing another example of a basic structure according to the present invention.

FIG. 2 is a circuit diagram illustrating another example of a basic structure according to the present invention. Similar with the basic structure of FIG. 1, an electrochemical pump cell 1 is made up of a solid electrolyte partition 2, a pair of electrodes 3 and 4 formed on the inner surface and the outer surface thereof, respectively, and a gas diffusion resistance layer 5 formed on the electrode 3. A power source 9 and a current detection means 10 are arranged between the output terminals 6 and 7 of the electrochemical pump cell 1.

On the inner surface and the outer surface of the solid electrolyte partition 2 made of a zirconia ceramic or the like, a further pair of electrodes 23 and 24 are provided, respectively, to form an electrochemical pump cell 21 combined with the gas diffusion layer 5 formed on the electrode 23. A fixed resistor 28 having a resistance corresponding to the sensitivity of the electrochemical pump cell 1 adjacent to the electrochemical pump cell 21 is connected to the output terminals 26 and 27 of the electrochemical pump cell 21 via a capacitor 29 in parallel with the cell.

In a sensor circuit having a configuration described above, when a specific voltage is applied from an alternate current power source 30 to the output terminals 26 and 27 of the cell 21 via a capacitor 31, almost no current flows to the cell 21 because the impedance of the cell 21 is very high at room temperature, and the current flows substantially only to the fixed resistor 28. Accordingly, if the measurement of the current is conducted by a second current detection means 11, the resistance value of the fixed resistor 28 may be read. Since the resistance value is set to correspond to the sensitivity of the electrochemical pump cell 1, the information relating the resistance value of the cell is stored in the second current detection means 11, thereby being capable of correcting the value of current in the case of actuation of the cell 21 at an elevated temperature based on the equation given below:

$$I_0 = K_n \times I_n$$

where, $I_0$ is a diffusion limiting current value after correcting the sensitivity, $K_n$ is a correction factor corresponding to the sensitivity of each cell, and $I_n$ is a value of current flowing to the current detection means 10.

With the method described above, correction is capable of effecting without influencing the current detection circuit of the electrochemical pump cell 1 and, even in the case of the electrochemical pump cell 21 for measuring an electromotive force, without influencing the electromotive force.

For instance, in FIG. 2, a potential difference (voltage) detection means 35 conducts the measurement of electromotive force corresponding to the difference of the oxygen concentration between the electrodes 23 and 24. The voltage applied to the electrochemical pump cell 1 is adjusted to control the electromotive force to a specific value.

The present invention is described in more detail in the examples given below referring to the drawings.

FIG. 3 shows a cross sectional view of a major part of a NOx sensor provided with a heater section, and an electric circuit thereof.

In FIG. 3, the NOx sensor includes a first internal space 42 and a second internal space 44 which are arranged separately with each other while positioning the first internal space 42 at the front end of the sensor element. A reference gas introduction space 47 as a reference gas existing space extends in the longitudinal direction of the sensor element independently from the first internal space 42 and from the second internal space 44. A first diffusion controlled section 41 which connects the first internal space 42 with an external measuring gas exiting space is arranged at the tip of the sensor element. The first internal space 42 and the second internal space 44 are connected with each other by a second diffusion controlled section 43.

The portion on a solid electrolyte partition 2 exposed to the first internal space 42 is provided with an inner Pump electrode 13. An outer pump electrode 14 is formed on the outer surface of the solid electrolyte partition 2 at an opposite site of the inner pump electrode 13. A main pump means (electrochemical pump cell) 1 is made up of these electrodes 13 and 14, and the solid electrolyte partition 2. Between the output terminals 6 and 7 of the main pump means 1, power source 9 and a current detection means 10 are arranged in the circuit, while connecting a fixed resistor 8 having a resistance value corresponding to the sensitivity of the main pump means 1 between the output terminals 6 and 7 in parallel.

The measuring electrode 45 is formed on a portion of the solid electrolyte partition 2 exposing to the second internal space 44, and a reference electrode 46 is formed on a portion of the solid electrolyte partition 2 exposing to the reference gas introduction space 47. A measuring pump means 20 is made up of a measuring electrode 45, the reference electrode 46, and the solid electrolyte partition 2. The circuit is structured to have a power source 17 and a current detection means 18 between the output terminals of the measuring pump means 20.

It should be noted that a heater section 40 is provided in the NOx sensor in such a manner that a heater 16 is buried while being surrounded by the solid electrolyte of the sensor. The heater generates heat by receiving power from a heater power source 48.

According to the NOx sensor thus configured, the measuring gas passes through the first diffusion controlled section 41 to enter the first internal space 42. By applying power from the power source 9 with a specific voltage to the pair of pump electrodes 13 and 14 formed on the inner surface and the outer surface of the solid electrolyte partition 2 made of a zirconia ceramic, respectively, facing with each other, the diffusion limiting current value of oxygen is determined by the current detection means 10. The NO which is not decomposed in the internal space 42 passes through the second diffusion controlled section 43 to enter the second internal space 44. By applying voltage from the power source 17 between the measuring electrode 45 and the reference electrode 46, NO is decomposed. The quantity of oxygen generated by the decomposition of NO is measured by a current detection means 18 to determine the quantity of NOx. When the value of resistance of resistor 8 is set to a value corresponding to the sensitivity to oxygen in the first internal space 42, or to the sensitivity to NOx gas in the second internal space 44, the value of pump current flowing to the main pump means 1, or the value of current flowing to the measuring pump means 3 is able to be corrected using the correction factor derived based on the measured value of the resistance of the resistor 8 using the current detection means 10 at room temperature. Particularly when the NOx concentration is corrected, the main pump means 1 does not decompose NO, so that the current flowing into the resistor 8 is independent of NOx measurement. As a result, the correction of NOx sensitivity or of offset may be effected at high accuracy.

FIG. 4 shows a cross sectional view of main part of another NOx sensor and the electric circuit thereof.

According to the example, the NOx sensor has only the first internal space 42 and does not have the second internal space 44. Instead of the second internal space 44, the second diffusion controlled section 43 made of gas diffusion resistance layer is formed. And further, as the measuring electrode 45, the one having a catalytic activity to decompose NOx gas is used.

At a portion of the solid electrolyte partition 2 exposing to the first internal space 42, the inner pump electrode 13 is formed, whereas, at a portion of the solid electrolyte partition 2 exposing to the reference gas introduction space 47, the outer pump electrode 14 which is common with the reference electrode is formed. The main pump means 1 is structured by these electrodes 13 and 14, and the solid electrolyte partition 2. A circuit having the power source 9 is formed between the output terminals of the main pump means 1. A different portion exposing to the first internal space 42, the measuring electrode 45 which has a catalytic activity to decompose NOx gas is formed. The second diffusion controlled section 43 comprising a gas diffusion resistance layer is formed covering the measuring electrode 45. At a portion of the solid electrolyte partition 2 exposing to the reference gas introduction space 47, the reference electrode 14 which is common with the outer pump electrode is formed. The measuring pump means 1 is structured by the measuring electrode 45, the reference electrode 14, and the solid electrolyte partition 2. A circuit having the power source 17 and the current detection means 10 is formed between the output terminals of the measuring pump means, while the fixed resistor 8 is connected between the output terminals of the electrochemical sensor cell in parallel with the cell.

According to the NOx sensor thus configured, the measuring gas passes through the first diffusion controlled section 41 to enter the first internal space 42. By applying power from the power source 9 with a specific voltage to the pair of pump electrodes 13 and 14 formed on the inner surface and the outer surface of the solid electrolyte partition 2 made of a zirconia ceramic, respectively, facing with each other, a quantity of oxygen within the first internal space 42 is brought to near a zero level. The NOx gas which Passes through the second diffusion controlled section 43 and arrives at the measuring electrode 45 having a catalytic activity is decomposed to generate oxygen. The quantity of oxygen is measured by the current detection means 10 to determine the quantity of NOx. When the value of resistance of resistor 8 is set to a value corresponding to the sensitivity to NOx, the NOx sensitivity is capable of being corrected at a high accuracy by measuring the value of the resistance of resistor 8 using the current detection means 10 at room temperature and by applying the correction factor derived from the measured value of the resistance of resistor 8.

FIG. 5 shows a cross sectional view of a main part of a diffusion limiting current type oxygen sensor and the electric circuit thereof.

According to the example, the inner pump electrode 13 is formed on a portion of the solid electrolyte partition 2 exposing to the internal space 52, and the outer pump electrode 14 is formed on the outer surface of the solid electrolyte partition 2 at a site opposite to the inner pump electrode 13. The main pump means 1 is structured by these electrodes 13 and 14, and the solid electrolyte partition 2. At a different exposed portion in the internal space 52 of the solid electrolyte partition 2, the measuring electrode 53 is formed. At a portion of the solid electrolyte partition 2 exposing to the reference gas introduction space 47, the reference electrode 54 is formed. The oxygen concentration cell is structured by the measuring electrode 53, the reference electrode 54, and the solid electrolyte partition 2. A circuit having the power source 9 and the current detection means 10 is formed between the output terminals of the main pump means 1, while connecting a series circuit of an alternate current power source 70, a resistor 56, and a capacitor 71 between the output terminals of the oxygen concentration cell, and also connecting a series circuit of a resistor 68 and a capacitor 69 between the output terminals of the oxygen concentration cell in parallel therewith.

According to the oxygen sensor thus configured, the measuring gas passes through the diffusion controlled section 51 to enter the internal space 52. By applying power from the power source 9 with a specific voltage to the pair of electrodes 13 and 14 formed on the inner surface and outer surface of the solid electrolyte partition 2 made of a zirconia ceramic, respectively, facing with each other, a quantity of oxygen within the internal space 52 is brought to a near zero level. The oxygen partial pressure in the internal space 52 is measured by a potential difference detection means 55 as the electromotive force which is determined by the ratio to the oxygen partial pressure in the reference gas introduction space 47 using the oxygen concentration cell structured by the electrodes 53 and 54 and by the solid electrolyte partition 2. Then, the voltage of the power source 9 is controlled to match the determined electromotive force with the predetermined value. During the course of measurement, the current flowing across the current detection means 10 corresponds to the oxygen concentration in the measuring gas. If the value of the resistance of a resistor 68 is set to a value corresponding to the sensitivity to oxygen gas, then it is possible that the value of the resistance of resistor 68 is measured by the potential difference (voltage) detection means 55 as a divided voltage of the alternate current power source 70 using the resistors 56 and 68, and that the sensitivity of measurement is matched to the sensitivity of individual sensors. The impedance of capacitors 69 and 71 is assumed as sufficiently small.

Figure 6:
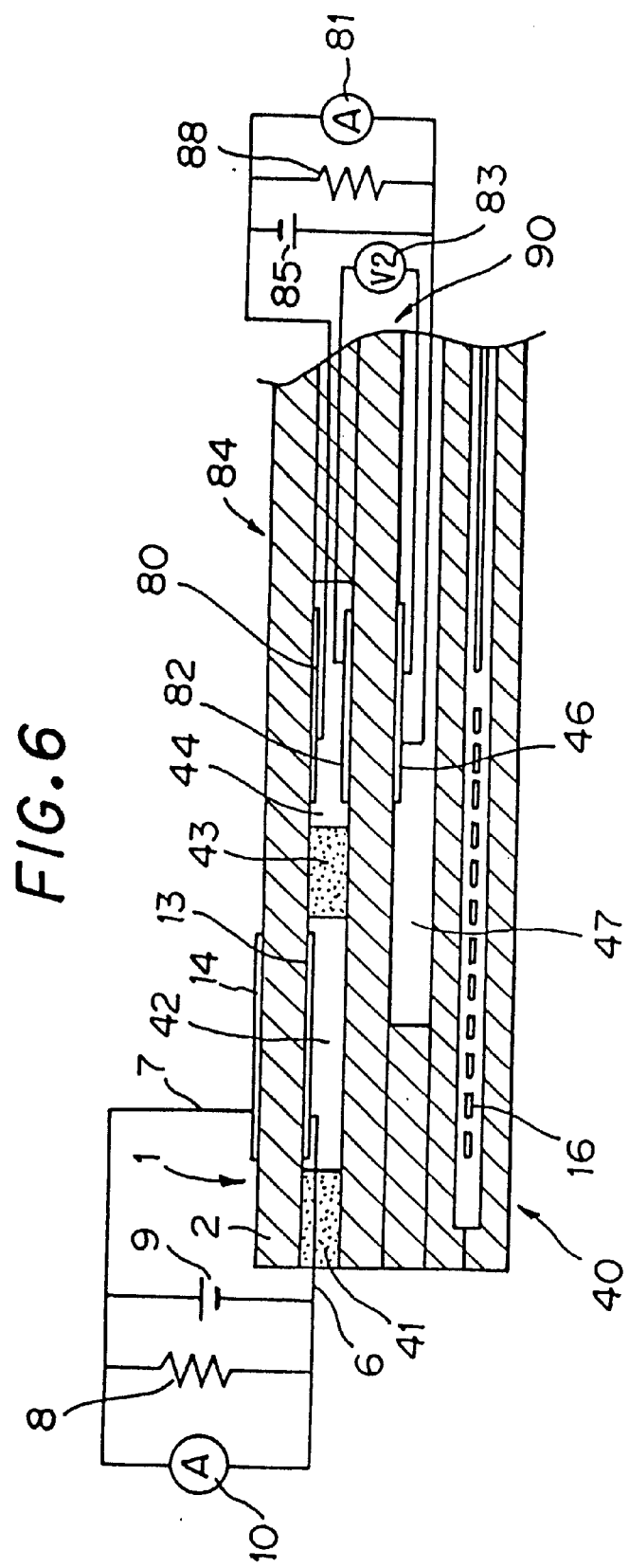
FIG. 6 is a cross sectional view of the main part of the sensor element and the circuit showing still another example according to the present invention.
Figure 7:
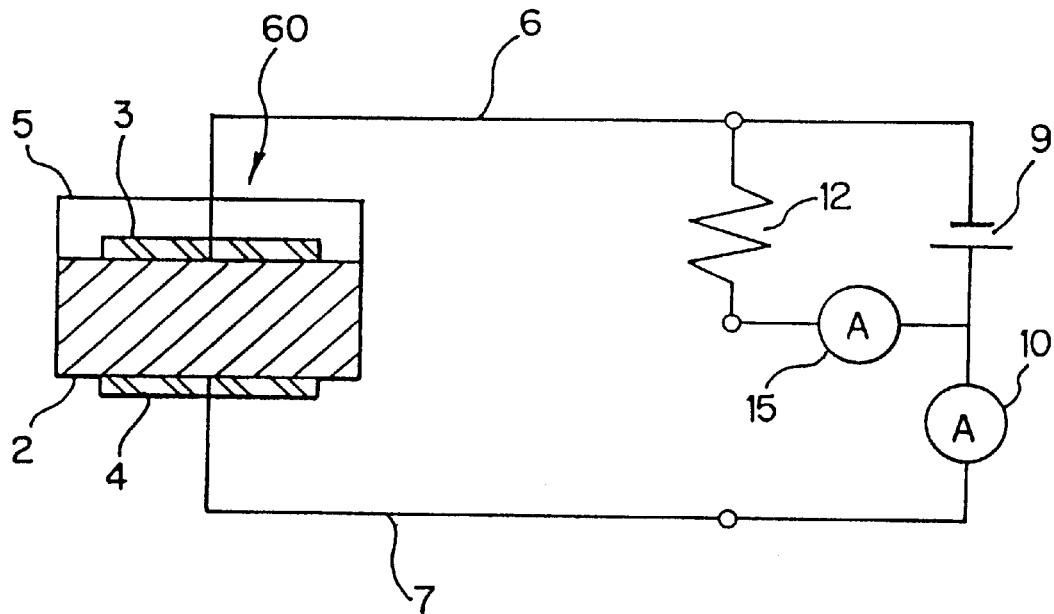
FIG. 7 is a cross sectional view showing a structural example of a conventional sensor element and the circuit.
Figure 8:
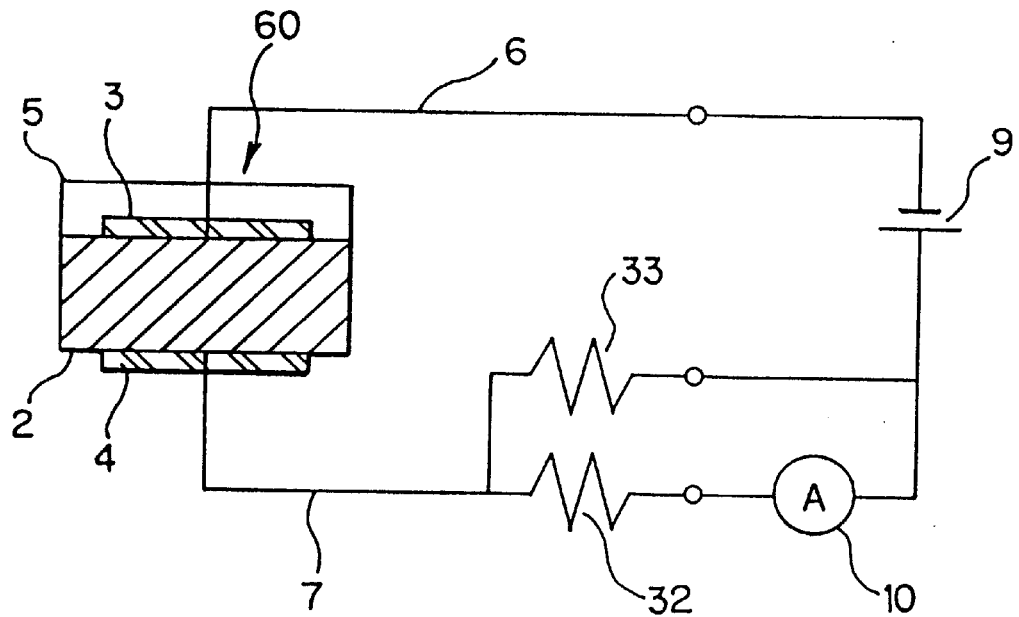
FIG. 8 is a cross sectional view of another structural example of a conventional sensor element and the circuit.

FIG. 6 shows a cross sectional view of main part of a sensor element provided with an auxiliary pump for further adjusting the fine variation of oxygen partial pressure in the measuring gas which has been subjected to the adjustment of oxygen partial pressure in the main pump cell 1, and conducting measurement of the NOx concentration by means of electromotive force. FIG. 6 also shows the electric circuit of the sensor element.

Compared with an example of FIG. 3, the example of FIG. 6 has basically the same configuration of the main pump 1 and the heater section 40, and differs in that an auxiliary pump 80 is added, that the NOx concentration is measured by means of electromotive force generated in a concentration detection means 90 which comprises a detection electrode 82 and the reference electrode 46.

According to this example, a circuit is structured by locating the power source 9 between the output terminals 6 and 7 of the main pump means 1, while connecting the fixed resistor 8 having a resistance corresponding to the sensitivity of the concentration detection means 90 between the output terminals 6 and 7 in parallel with the Power source.

A portion of the solid electrolyte partition 2 exposed to the second internal space 44 is provided with the detection electrode 82. A portion of the solid electrolyte partition 2 exposed to the reference gas introduction space 47 is provided with the reference electrode 46. The concentration detection means 90 is structured by the detection electrode 82, the reference electrode 46, and the solid electrolyte partition 2. Also, a different portion in the second internal space 44 is provided with the auxiliary pump electrode 80. The auxiliary pump means 84 is structured by the auxiliary pump electrode 80, the reference electrode 46 formed in the reference gas introduction space 47, and the solid electrolyte partition 2. A potential difference detection means 83 is arranged between the output terminals of the concentration detection means 90. A circuit having the power source 85 is formed between the output terminals of the auxiliary pump means 84, while connecting a fixed resistor 88 having a resistance corresponding to the offset value of the concentration detection means 90 in parallel therewith.

According to the NOx sensor thus configured, the measuring gas passes through the first diffusion controlled section 41 to enter the first internal space 42. By applying a predetermined voltage from the power source 9 to the pair of electrodes 13 and 14 located on the inner surface and the outer surface of the solid electrolyte partition 2, respectively, facing with each other, the oxygen pumping action is induced, which pumping action controls the oxygen partial pressure to a predetermined level at which NO does not decompose. The measuring gas in which the oxygen partial pressure is controlled to a Predetermined level passes through the second diffusion controlled section 43 to enter the second internal space 44. By applying voltage from the power source 85 between the auxiliary pump electrode 80 and the reference electrode 46, the measuring gas is adjusted to further a low level of oxygen partial pressure. The NO is decomposed on the detection electrode 82 which has an ability of NO decomposition and which is formed in the second internal space 44. Thus, the NOx concentration is determined by determining the oxygen generated along with the decomposition of NO by means of the potential difference detection means 83.

When the resistance of the resistor 8 is set to a value corresponding to the sensitivity (the reduction rate of electromotive force relative to the NOx concentration) of the concentration detection means 90, and when the resistance of the resistor 88 is set to a value corresponding to the offset value of the concentration detection means 90, the measurement of resistance of the resistor 8 and of the resistor 88 by the current detection means 10 and by the current detection means 81, respectively, allows the setting of the correction factor to an optimum value to the sensor before actuating thereof. As a result, the NOx concentration is determined at higher accuracy.

The description given above employed a configuration that an element has two electrochemical pump cells with two resistors. Nevertheless, the resistor may be other RLC element. In addition, the number of RLC elements is arbitrarily chosen responding to the number of pump cells.

As described above, according to the present invention, a small number of terminals conduct correction of the sensitivity of individual sensors, while improving the reliability and avoiding cost increase. These advantages are significantly useful for industrial practice.

What is claimed is:

1. A gas sensor for measuring a quantity of a specific target component in a measuring gas comprising:

main pump means including an electrochemical pump cell comprising a solid electrolyte partition exposed to external space, an inner pump electrode and an outer pump electrode formed on the inner surface and the outer surface of the solid electrolyte partition, respectively, and said main pump means treating oxygen contained in a first internal space in the measuring gas introduced from said external space by pumping processing on the basis of a control voltage applied between said inner pump electrode and said outer pump electrode; and electric signal conversion means for generating an electric signal corresponding to the quantity of oxygen generated by decomposition or reduction of a target component contained in the measuring gas after having been treated by the pumping processing by said main pump means in which the solid electrolyte partition has a pair of detection electrodes formed with one of said pair of the detection electrodes exposed to the atmosphere of a second internal space whose oxygen concentration is controlled by the main pump means in the first internal space and the other of the detection electrodes exposed to an external atmosphere, wherein:
- a resistor capable of calculating or estimating a corrected value for outputs of said sensor from a value of resistance at room temperature is connected in parallel with output terminals of either said electrochemical pump cell or said electric signal conversion means.

2. A gas sensor as claimed in claim 1, wherein said electric signal conversion means comprises:

measuring pump means for conducting pumping processing of oxygen generated by decomposition or reduction of target components contained in the measuring gas after having been treated by the pumping processing by said main pump means on the basis of a measuring voltage applied between said pair of detection electrodes; and current detection means for detecting a pump current generated in the measuring pump means, wherein:
- a quantity of the specific component in the measuring gas is determined on the basis of the pump current detected by the current detection means.

3. A gas sensor as claimed in claim 1, wherein said electric signal conversion means comprises:

concentration detection means for generating an electromotive force corresponding to the difference between a quantity of oxygen generated by decomposition or reduction of the target component contained in the measuring gas after having been treated by the pumping processing by said main pump means and a quantity of oxygen contained in a reference gas on the side of the detection electrode formed on the side of the external atmosphere; and voltage detection means for detecting the electromotive force generated in the concentration detection means, wherein:
- a quantity of the specific component in the measuring gas is determined on the basis of the electromotive force detected by the voltage detection means.

4. A method of measuring a quantity of specific component in a measuring gas comprising:

using main pump means of a sensor including an electrochemical pump cell comprising a solid electrolyte partition exposed to external space, an inner pump electrode and an outer pump electrode formed on the inner surface and the outer surface of the solid electrolyte partition, respectively, to control oxygen gas partial pressure in the measuring gas in a first internal space to a predetermined value by conducting pumping processing of the oxygen contained in the measuring gas introduced in said first internal space from the external space on the basis of a control voltage applied between said inner pump electrode and said outer pump electrode;

converting a target component contained in the measuring gas after having been treated by pumping processing by said main pump means using electric signal conversion means having a pair of detection electrodes formed with one of said pair of the detection electrodes exposed to the atmosphere of a second internal space whose oxygen concentration is controlled by the main pump means in the first internal space and the other of the detection electrodes exposed to an external atmosphere, said detecting electrodes producing an electric signal corresponding to a quantity of oxygen generated either by decomposition or reduction; and measuring a quantity of a specific component in the measuring gas on the basis of an electric signal coming from said electric signal conversion means, wherein:
- a resistor which has a predetermined electric characteristic value corresponding to a characteristic value of said electric signal is connected in parallel with the output terminals of either said electrochemical pump cell or said electric signal conversion means;

setting of a output correction of said electric signal conversion means at an elevated temperature is carried out at room temperature by determining the electric characteristic value of said resistor in a state that ion conductivity of solid electrolyte is removed; and the output of said electric signal conversion means is corrected on the basis of the determined electric characteristic value of said resistor.

* * * * *